United States Patent [19]

Geyer et al.

[11] Patent Number: 5,466,865
[45] Date of Patent: * Nov. 14, 1995

[54] NEOMORPHIC IBUPROFEN AND METHODS OF USING SAME

[75] Inventors: Robert P. Geyer, Brookline, Mass.; Vinod V. Tuliani, Media, Pa.

[73] Assignee: Ibah, Inc., Blue Bell, Pa.

[*] Notice: The portion of the term of this patent subsequent to May 18, 2070, has been disclaimed.

[21] Appl. No.: 169,672

[22] Filed: Dec. 17, 1993

Related U.S. Application Data

[63] Continuation-in-part of Ser. No. 87,573, Jul. 2, 1993, Pat. No. 5,310,961, and a continuation-in-part of Ser. No. 86,922, Jul. 2, 1993, Pat. No. 5,310,960.

[51] Int. Cl.$^6$ .................................................. C07C 53/134
[52] U.S. Cl. ............................................................ 562/496
[58] Field of Search ............................... 562/496; 514/568

[56] References Cited

U.S. PATENT DOCUMENTS

| | | | |
|---|---|---|---|
| 3,625,711 | 12/1971 | Eisenstadt | 99/141 A |
| 4,049,699 | 9/1977 | Sinkula | 560/105 |
| 4,049,700 | 9/1977 | Sinkula | 560/105 |
| 4,361,580 | 11/1982 | Peck et al. | 424/287 |
| 4,726,966 | 2/1988 | Kawashima et al. | 427/213.36 |
| 4,835,186 | 5/1989 | Reuter et al. | 514/570 |
| 4,835,188 | 5/1989 | Ho et al. | 514/570 |
| 4,916,161 | 4/1990 | Patell | 514/570 |
| 5,191,114 | 3/1993 | Chen | 562/496 |

OTHER PUBLICATIONS

Vinod Labhasetwart, et al., *Studies On Some Crystalline Forms of Ibuprofen,* Drug Development and Industrial Pharmacy, 19(6), 631–641 (1993).

*Primary Examiner*—Paul J. Killos
*Attorney, Agent, or Firm*—Woodcock Washburn Kurtz Mackiewicz & Norris

[57] ABSTRACT

A novel neomorphic form of ibuprofen, processes for preparing the ibuprofen, and method for administering the ibuprofen are provided. The neomorphic form is characterized by having a distinctively less bitter taste and causes less burning sensation upon swallowing. The neomorphic form of ibuprofen contains an amorphous ibuprofen. Tests indicate that the neomorphic form is less irritating to the gastrointestinal tract of animals upon administration.

30 Claims, 5 Drawing Sheets

NEOMORPHIC IBUPROFEN AND METHODS OF USING SAME

This is a continuation-in-part of application Ser. No. 08/087,573 filed Jul. 2, 1993, now U.S. Pat. No. 5,310,961, and a continuation-in-part of application Ser. No. 08/086,922 filed Jul. 2, 1993, now U.S. Pat. No. 5,310,960.

FIELD OF THE INVENTION

The present invention relates to a novel form of ibuprofen characterized by having a distinctively less bitter and acidic taste than is normally associated with conventional ibuprofen. More specifically, the invention relates to a novel neomorphic form of ibuprofen. Tests indicate that the neomorphic form of ibuprofen is less irritating upon administration to an animal in comparison to conventional ibuprofen.

BACKGROUND OF THE INVENTION

Ibuprofen is one of the most popular non-steroidal anti-inflammatory drugs available today. Ibuprofen is recommended for treating animals, particularly humans, as an anti-inflammatory, analgesic, and anti-pyretic drug. Ibuprofen is commonly used for reducing the pain associated with headaches and muscle aches, for reducing fevers, and for reducing inflammation. Ibuprofen is also commonly prescribed for the treatment of arthritis. Conventional ibuprofen is known to have a distinctly bitter, acidic, foul taste and to cause a burning sensation in the mouth and throat upon oral administration. Therefore, various attempts have been made to mask the taste of ibuprofen, the most common being to coat the ibuprofen in a tablet form for oral administration without chewing, usually accompanied with liquids to aid the swallowing, thus hiding the unpleasant taste of the free acid.

Unfortunately, a substantial portion of the population cannot swallow a tablet form of a drug and this is particularly true in the young and aged. These individuals commonly take such drugs in a liquid form, however the foul taste of ibuprofen in liquid form will most likely preclude compliance among these individuals.

Various attempts have been made to mask the taste of ibuprofen. The most common attempts incorporate the use of taste-masking agents with the ibuprofen, accompanied in many cases by costly production procedures. Examples of these prior efforts include admixing hydroxypropyl methylcellulose phthalate with the ibuprofen in a wet granulation process as shown in U.S. Pat. No. 4,916,161; spray drying a dispersion of ibuprofen, ethyl cellulose, and a plasticizer as shown in U.S. Pat. No. 4,835,188; dissolving ibuprofen with acrylic acid resin in an organic solvent and water to provide a granulated ibuprofen as shown in U.S. Pat. No. 4,726,966; and spray drying ibuprofen in a suspension of colloidal silica, alcohol, and cellulose acetate as shown in U.S. Pat. No. 4,835,186. Various attempts have also been made to alter the chemical structure of ibuprofen to a form that has a less objectionable taste as shown in U.S. Pat. Nos. 4,049,699 and 4,361,580, however the utility of these forms remains to be determined.

Conventional ibuprofen having a crystalline structure is also very irritating to the gastrointestinal tract of an animal. Continuous or high quantity dosing via oral administration of conventional crystalline ibuprofen can cause stomach irritation and even ulceration. This side effect of conventional crystalline ibuprofen limits its utility with a substantial portion of potential users.

There still exists a need in the art to develop a taste-masked form of ibuprofen which can be prepared easily and does not require the additional blending of specific amounts of certain taste-masking agents. Further, there exists a need to develop an ibuprofen form that is less irritating to the gastrointestinal tract of an animal.

SUMMARY OF THE INVENTION

The present invention provides an improved tasting neomorphic ibuprofen composition, methods for its preparation, and methods for its administration. This neomorphic ibuprofen composition is characterized by containing ibuprofen having an amorphous structure. By "amorphous" is meant that the ibuprofen has no defined crystalline structure characteristic of conventional ibuprofen. This characteristic is easily determined by visual inspection using microscopic means and by birefringence testing, by which the amorphous ibuprofen within the neomorphic ibuprofen composition exhibits substantially no birefringence while the conventional crystalline form of ibuprofen exhibits marked birefringence.

The particles of the neomorphic ibuprofen composition, prepared at temperatures of from about 0°–65° C. using kinetic energy as described later, generally have a roughly irregular particle shape; the particles are substantially equi-axial and the number average ratio of the longer axis to the shorter axis of the particles is generally less than about 3:1, preferably less than about 3:2. The neomorphic ibuprofen composition particles, on a number average basis, preferably have an averaged particle size of greater than about 100 microns and generally less than about 500 microns. By "averaged particle size" is meant the average of the diameter of the particles along their longest axis and shortest axis. The ibuprofen particles are thus distinct morphologically from conventional ibuprofen which is characterized by having a rod-like crystalline structure, being usually about 100 microns in length and up to about 20 microns in width, and thus have an averaged particle size of less than about 100 microns, although this can vary depending upon the particular manufacturer.

The neomorphic ibuprofen compositions can be prepared by various methods. Common to the methods is the alteration of the normal resolidification of the ibuprofen from an ibuprofen melt, which resolidification ordinarily yields crystalline ibuprofen. The methods are performed by first providing ibuprofen in a supercooled state. Typically, the ibuprofen is heated past its melting point resulting in a molten ibuprofen. This molten ibuprofen is then cooled below its melting point while maintaining the molten condition, thus achieving a supercooled ibuprofen state.

One method for the resolidification of the supercooled ibuprofen into the improved tasting ibuprofen requires some form of energy, in the form of kinetic energy, to be imparted into the supercooled ibuprofen. The neomorphic ibuprofen composition containing the amorphous ibuprofen is then recovered. It is preferred to continue the application of the kinetic energy until a majority of the ibuprofen is converted to the amorphous form. This method can be conducted at various temperatures below the melting point of the ibuprofen.

A further method for the preparation of the neomorphic ibuprofen compositions, conducted at any process temperature, is to provide the molten, supercooled ibuprofen in a fluid that disperses the supercooled ibuprofen as a discrete molten phase, preferably an internal dispersed phase. Kinetic energy is imparted into the mixture containing the dispersed ibuprofen to convert the supercooled ibuprofen into the neomorphic ibuprofen composition containing solid amorphous ibuprofen, and the composition is then recovered. The process can be operated in a batch-wise or continuous fashion with the recycling of the dispersant fluid.

The preparation of the neomorphic ibuprofen compositions can also be accomplished at processing temperatures of below about 0° C. When the supercooled ibuprofen is brought to such low processing temperatures, the application of kinetic energy for the resolidification of the ibuprofen into the neomorphic ibuprofen composition containing amorphous ibuprofen is optional. The neomorphic ibuprofen composition is produced upon resolidification and is recovered.

The preparation of the neomorphic ibuprofen composition can be aided by the "seeding" of the supercooled ibuprofen with amorphous ibuprofen. This technique is particularly preferred for low temperature processing.

This invention further relates to methods of treating a patient for an inflammatory condition by administering an effective quantity of the neomorphic ibuprofen. Since the neomorphic ibuprofen composition of the present invention, containing the amorphous ibuprofen, is believed to be less irritating to the gastrointestinal tract of an animal to which it is administered, preferred methods of administration include any method in which the ibuprofen comes into contact with the gastrointestinal tract or a mucosal membrane of the animal. Such methods include mucosal administration, preferably oral, rectal, and vaginal administration.

DETAILED DESCRIPTION OF THE INVENTION

The present invention relates to a neomorphic form of the non-steroidal anti-inflammatory drug (NSAID) ibuprofen, preparatory methods for making the same, and methods of administering the same. Conventional ibuprofen is characterized by its bitter taste upon mastication, burning sensation upon swallowing, and irritation to the animal upon administration, most notably, the gastrointestinal tract. The neomorphic form of ibuprofen of the present invention is characterized by having a bland or neutral taste, producing a greatly reduced burning sensation felt at the back of the throat upon swallowing of the drug, and causing less irritation to the gastrointestinal tract upon administration. Thus the neomorphic form is ideally suited for administration of ibuprofen in any format, especially in a format other than in a taste-coated tablet that is to be swallowed without contact of the drug with the mouth or throat. Such administration forms include powders or tablets that can be chewed, liquid suspensions for drinking, or in some form that allows for the contacting of the ibuprofen with the gastrointestinal tract or mucosal membrane of an animal.

Conventional ibuprofen, as used herein, refers to the chemical compound that has been chemically named ±2-(p-isobutylphenyl)propionic acid, 2-(4-isobutylphenyl)propionic acid, p-(iso-butyl)hydrotropic acid, and α-methyl-α-(p-isobutylphenyl)acetic acid, either as a racemic mixture or as either of its + or − isomers.

The present neomorphic form of ibuprofen is chemically similar to the conventional form of ibuprofen, but is different with respect to its physical characteristics and taste characteristics.

The neomorphic ibuprofen compositions of the present invention can be produced in a wide variety of ways employing common physical and chemical characteristics of ibuprofen. The production processes take advantage of the supercooled state of ibuprofen and the ability of ibuprofen to resolidify into an amorphous form under conditions that inhibit recrystallization.

Various methods for the preparation of the neomorphic form of ibuprofen of the present invention are set forth in U.S. Pat. No. 5,310,961 filed Jul. 2, 1993 entitled Neomorphic Ibuprofen and U.S. Pat. No. 5,310,960 entitled Low Temperature Process for Preparing Neomorphic Ibuprofen, both of which are assigned to the assignee of the present application and both of which are incorporated herein by reference in their entireties.

In one method of production the resolidification requires the application of energy to the molten, supercooled ibuprofen. In broad terms, the process encompasses providing ibuprofen in a supercooled state, imparting energy, preferably kinetic energy, into the molten ibuprofen for a time and intensity sufficient to convert the molten ibuprofen into a solid neomorphic ibuprofen composition containing amorphous ibuprofen, and recovering the resultant product.

In this method the ibuprofen is heated above its melting point of about 74°–77° C., so the heating is preferably above about 75° C., more preferably from about 75°–80° C., resulting in a molten ibuprofen. This molten ibuprofen is then cooled to below its melting point to a process temperature of below about 65° C. to take advantage of the lower viscosity at elevated temperatures, and preferably the temperature is maintained below about 60° C., more preferably below about 55° C., due to the release of heat upon resolidification and thus the possibility of the ibuprofen again passing into the molten state as kinetic energy is supplied. The resolidification can, of course, be conducted at various lower temperatures, the lower temperature being limited only by practical processing limitations. However, the processing temperature is preferably above about −70° C., or above about −40° C., more preferably above about −30° C. In general practice, the process temperature is from about −20° C. to about 65° C., preferably from about 0° C. to about 45° C., more preferably from 0° C. to 35° C., and most preferably from 0° C. to 25° C. Preferably, agitation is minimized during the cooling of the molten ibuprofen to the supercooled state and to the process temperature to minimize any premature resolidification into the crystalline state.

The type of kinetic energy imparted into the supercooled ibuprofen will be dependent upon the type of processing system used to handle the manufacture. The kinetic energy is applied to the supercooled ibuprofen for a time and intensity sufficient to cause resolidification into the neomorphic form. It is preferred that the kinetic energy be applied for a time and intensity sufficient for at least about 50 weight percent, preferably at least about 70 weight percent, more preferably at least about 90 weight percent, and most preferably at least about 95 weight percent, of the supercooled ibuprofen to be solidified into the amorphous state. It is noted that if the kinetic energy is discontinued during the resolidification process, or if the energy is not sufficiently intense, then the supercooled ibuprofen can recrystallize on its own into the conventional crystalline form of ibuprofen having unpleasant taste characteristics, this effect being more noticeable at the higher processing temperatures.

It is to be understood that the neomorphic ibuprofen compositions produced by the methods of the present invention may contain various polymorphs of ibuprofen including not only the amorphous form but also, in some instances, remaining crystalline ibuprofen. As noted above, it is preferred to arrive at a neomorphic ibuprofen composition containing at least about 50, preferably at least about 70, more preferably at least about 90, and even more preferably at least about 95, weight percent of the amorphous form based upon the total amount of ibuprofen. Thus, the term neomorphic ibuprofen composition encompasses the total amount of ibuprofen found in the composition. Those skilled in the art would be able to approximate the amount of amorphous ibuprofen found in the neomorphic composition by such various means as scanning electron microscopy, differential scanning calorimetry, birefringence analysis, x-ray diffraction and taste.

Figure 1:
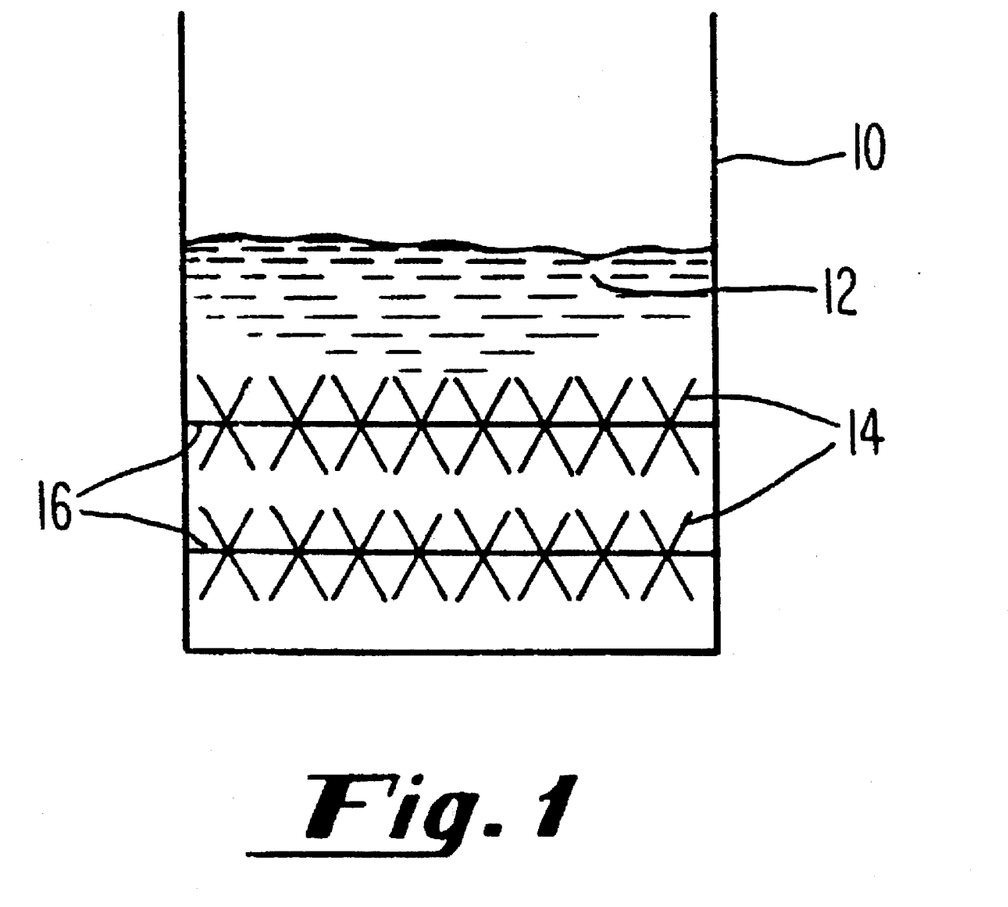
FIG. 1 is a cut-away view of a reaction vessel for performing the methods of the present invention.

Manufacture of the neomorphic ibuprofen compositions in a batch-wise manner can be accomplished by containing the supercooled ibuprofen in an appropriate vessel. Preferred vessels include plastic vessels capable of transmitting the kinetic energy effectively to the supercooled ibuprofen and having a surface which favors the production of the amorphous ibuprofen. The kinetic energy can then take the form of, for example, physically striking the vessel walls or vigorously stirring or striking the supercooled ibuprofen for a time and intensity sufficient to form the amorphous ibuprofen. The vessel can be equipped with "seeding surfaces" made of appropriate materials which can take the form of any type of exposed surface inside the vessel upon which the supercooled ibuprofen can resolidify. As shown in FIG. 1, the vessel 10 containing the supercooled ibuprofen 12 can contain seeding surfaces 14, shown here as rod-like protrusions supported by bars 16.

A further process for the production of neomorphic ibuprofen compositions is to disperse ibuprofen, either before or after attaining the supercooled state, in a dispersing fluid. Particulate ibuprofen can be added to the dispersing fluid and this dispersion can be brought to a temperature to melt the ibuprofen, or the dispersing fluid can be admixed to the molten or supercooled ibuprofen. The dispersing fluid can be broadly defined as any fluid in which the molten ibuprofen can be dispersed without materially altering the chemical nature of the ibuprofen and in which the ibuprofen has a relatively low solubility. Kinetic energy is then imparted into this supercooled ibuprofen dispersion for a time and intensity sufficient to convert the ibuprofen into its neomorphic form. The neomorphic ibuprofen is then recovered by, for example, filtering or evaporating the dispersing fluid. The process can proceed in batch-wise or continuous fashion. It is preferred that the kinetic energy supplied be in the form of physically shaking a vessel containing the dispersion mixture, or by stirring the dispersion, or by pumping the mixture into a barrier. Suitable dispersing fluids include glycerol and water, among others. The dispersing fluid can be recycled back into the production process after it is separated from the neomorphic ibuprofen. The yields of the amorphous ibuprofen within the neomorphic ibuprofen composition thus produced are similar to the yields for the kinetic energy process without the dispersing fluid.

Figure 2:
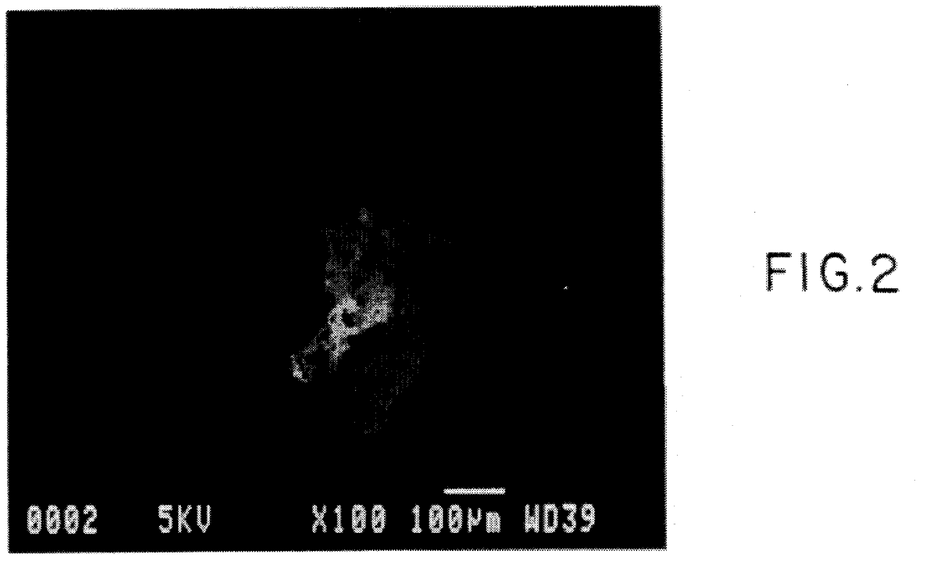
FIG. 2 is a photomicrograph of the neomorphic ibuprofen of the present invention taken at 100× magnification using a scanning electron microscope with a line legend of 100 microns.
Figure 3:
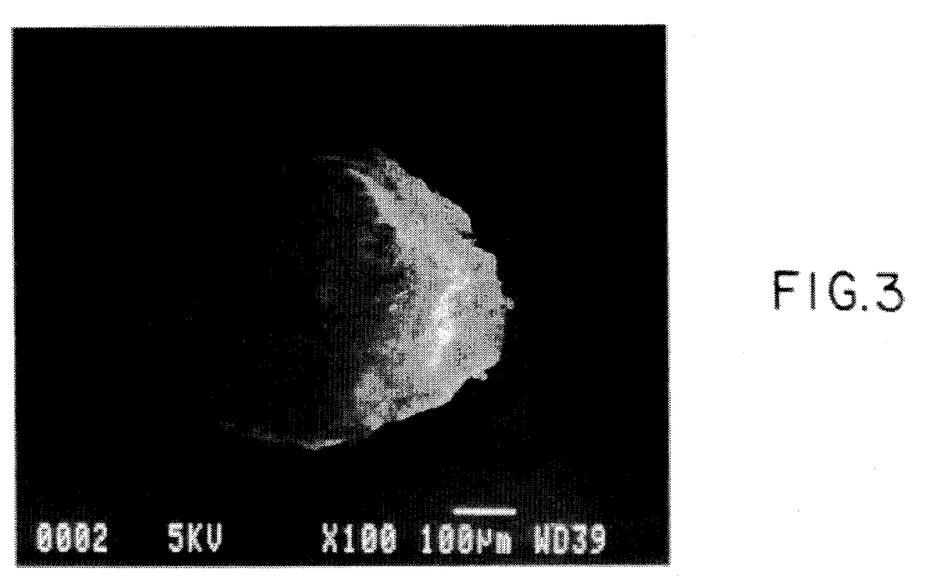
FIG. 3 is a second photomicrograph of the neomorphic ibuprofen of the present invention taken at 100× magnification using a scanning electron microscope with a line legend of 100 microns.
Figure 4:
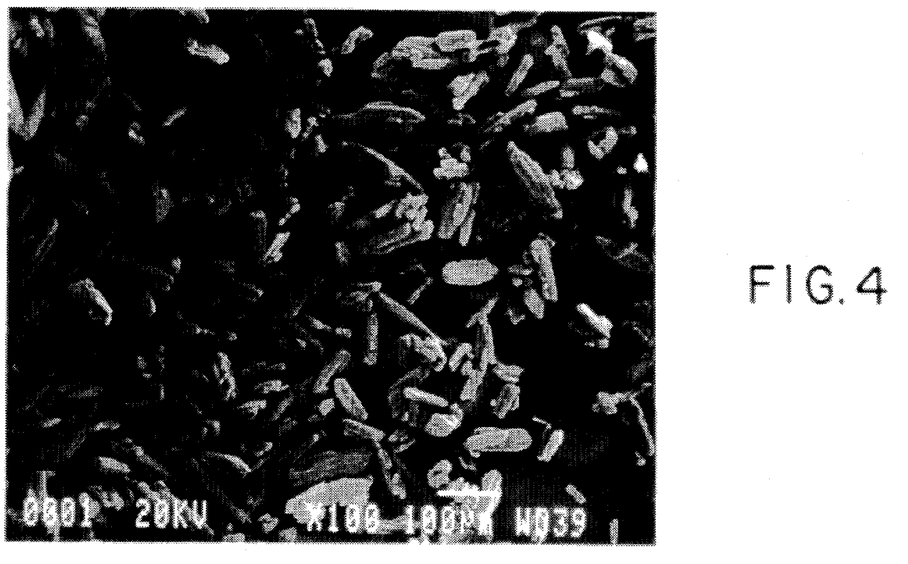
FIG. 4 is a photomicrograph of conventional ibuprofen taken at 100× magnification using a scanning electron microscope with a line legend of 100 microns.

The neomorphic ibuprofen compositions prepared by the processes described above can be described by their distinguishing physical features in relation to conventional ibuprofen. Conventional ibuprofen is characterized by its crystalline structure, while the neomorphic ibuprofen compositions contain ibuprofen having an amorphous structure. The neomorphic ibuprofen compositions containing the amorphous ibuprofen are generally characterized by particles having a roughly irregular shape as shown in FIGS. 2–3. Generally, the ratio of the length of the longest axis to the shortest axis of the amorphous ibuprofen particles is less than about 3:1, preferably less than about 2:1, more preferably less than about 1.5:1, on a number average basis. The amorphous form of ibuprofen is distinct from the conventional form of ibuprofen, FIG. 4, which has a rod-like crystalline structure with a length of about 100 microns and a width of about 20 microns, and thus has an averaged particle size of about 60 microns on a number average basis and a longest:shortest axis ratio of about 5:1. The amorphous ibuprofen particles preferably have an averaged particle size of greater than about 100 microns, preferably greater than about 200 microns, more preferably greater than about 300 microns, and generally in the range of from about 100 to about 600 microns, preferably from about 200 to about 600 microns, on a number average basis. However, if preferred, the neomorphic ibuprofen compositions can be comminuted to smaller average particle sizes of below about 150 microns, or below about 100 microns, and in some cases below about 50 microns.

The "averaged particle size" is determined by taking the average of the measurements of the length of the longest axis and the shortest axis of the particle. It is noted that those skilled in the art are able to determine average particle sizes and number average ratios by conventional methods such as microscopic analysis.

Figure 5:
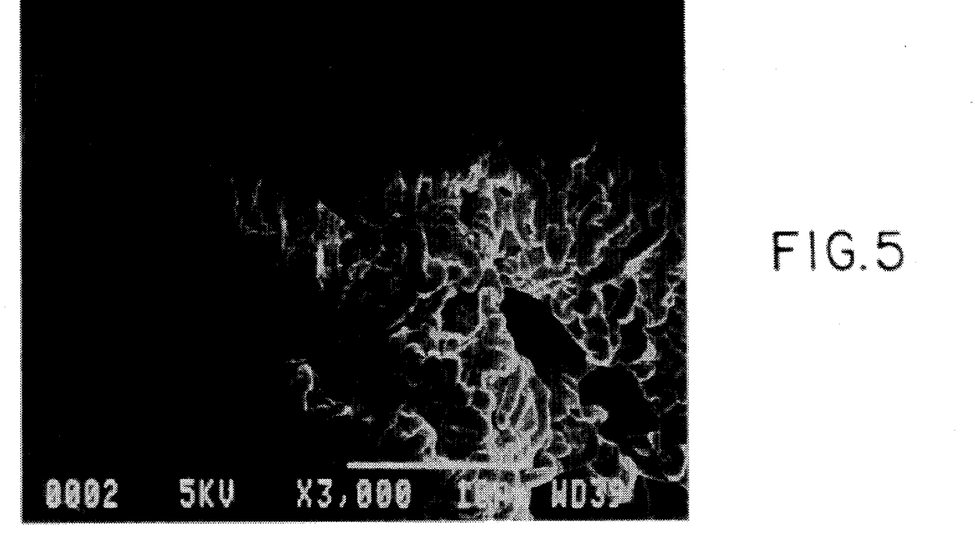
FIG. 5 is a photomicrograph of the neomorphic ibuprofen of the present invention taken at 3,000× magnification using a scanning electron microscope with a line legend of 10 microns.
Figure 6:
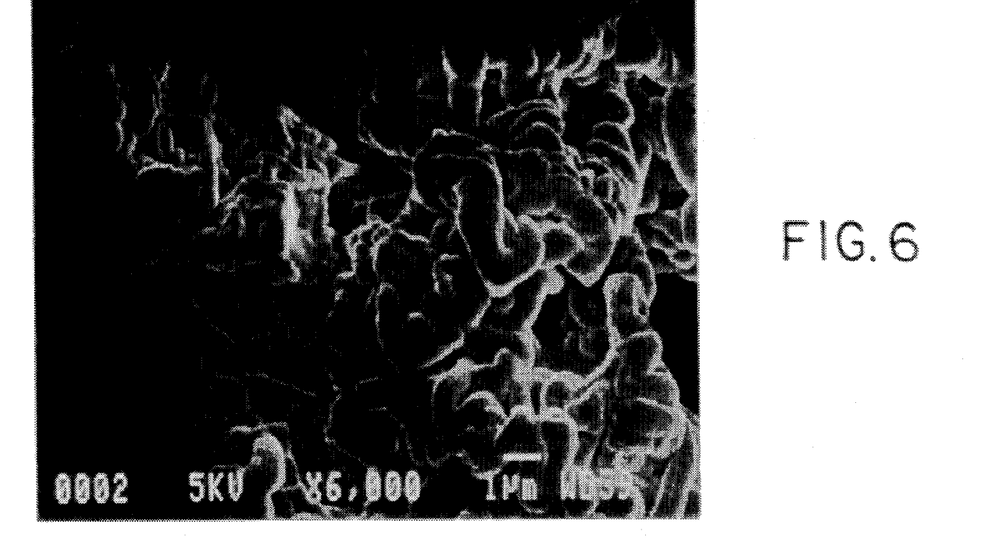
FIG. 6 is a photomicrograph of the neomorphic ibuprofen of the present invention taken at 6,000× magnification using a scanning electron microscope with a line legend of 1 micron.
Figure 7:
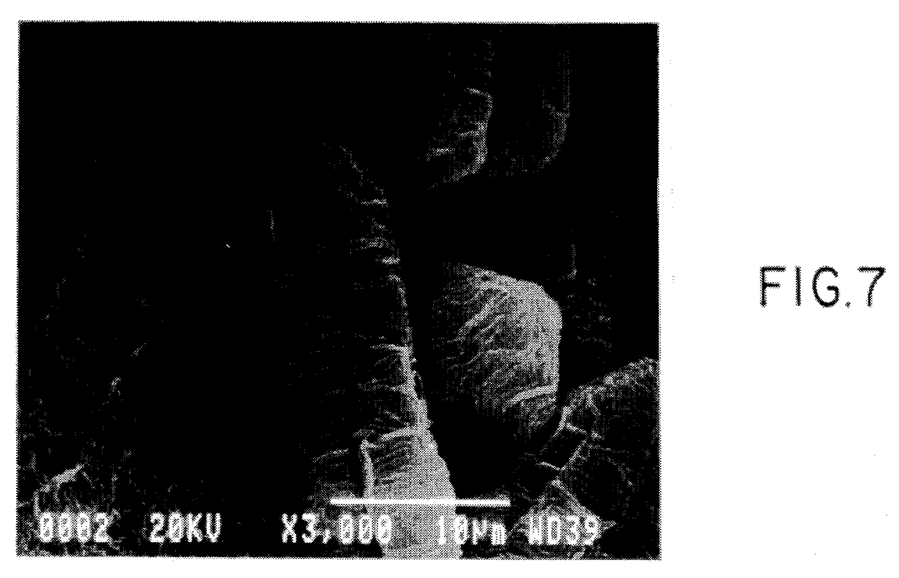
FIG. 7 is a photomicrograph of conventional ibuprofen taken at 3,000× magnification using a scanning electron microscope with a line legend of 10 microns.
Figure 8:
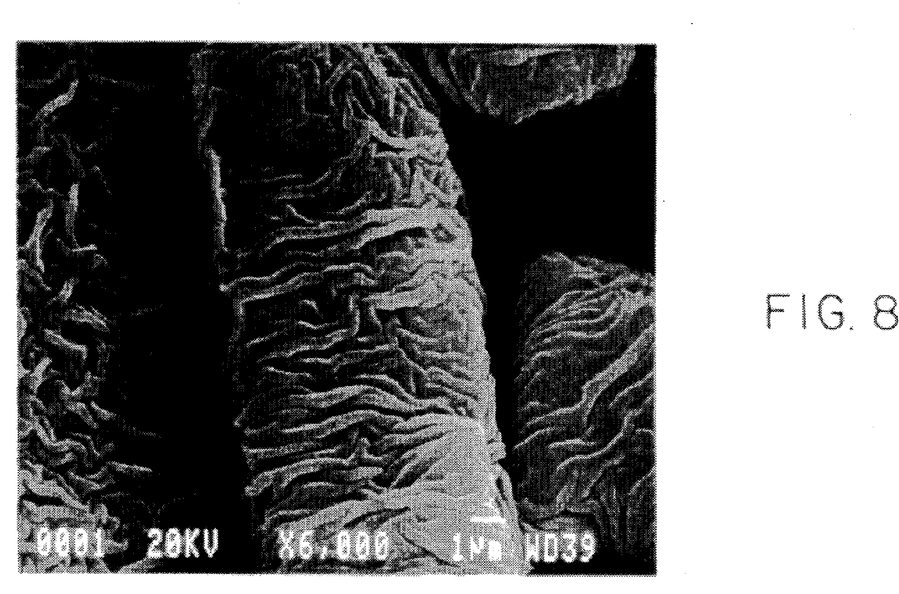
FIG. 8 is a photomicrograph of conventional ibuprofen taken at 6,000× magnification using a scanning electron microscope with a line legend of 1 micron.

The surface of an amorphous ibuprofen particle under the scanning electron microscope at a magnification of 3000× and 6000×, FIGS. 5 and 6, respectively, is fused and irregular. The surface is characterized by a multitude of grooves. The grooves on the surface of the amorphous ibuprofen particles produced in accordance with the methods set forth above are approximately 1–3 microns in width and approximately 5–15 microns in length and are in a contorted, twisted, nonorderly pattern. The amorphous ibuprofen particles also frequently contain "pores" on the surface. The surface of conventional ibuprofen under the same magnification, FIGS. 7 and 8, respectively, is ordered and regular. The grooves on the surface of conventional ibuprofen crystals are approximately 0.2–0.6 microns in width and appear to generally extend around the circumference of the particle in an orderly fashion perpendicular to the long axis.

The neomorphic ibuprofen compositions of the present invention, containing the amorphous ibuprofen, can also be prepared by processes not requiring the application of kinetic energy. The ibuprofen is first brought to the molten state. This molten ibuprofen is then cooled to below its melting point to a process temperature of at least below 0° C., preferably below about −10° C., more preferably below −20° C. while maintaining the supercooled state. The lower limit for the process temperature is generally a function of the processing capabilities, and is generally as low as about −70° C., preferably as low as −60° C., and more preferably −40° C. Therefore, the process temperature can be conveniently set at about −70° C. to 0° C., preferably −60° C. to −10° C., more preferably −40° C. to −20° C. The supercooled ibuprofen is a highly viscous liquid at these process temperatures. Preferably, agitation is minimized during the cooling of the molten ibuprofen to the supercooled state and to the process temperature to minimize any premature resolidification into the crystalline state. The supercooled ibuprofen is then allowed to resolidify at the process temperature into the neomorphic ibuprofen composition without the need for the application of kinetic energy. The low processing temperature inhibits the recrystallization of the ibuprofen to its normal crystalline form. The neomorphic ibuprofen composition is then recovered. This process yields the amorphous form of ibuprofen in high yields of at least about 50 weight percent, preferably at least about 70 weight percent, more preferably at least about 90 weight percent, and most preferably at least about 95 weight percent of the neomorphic ibuprofen composition. The application of kinetic energy can be used to aid in the resolidification process.

As to all processes for the manufacture of the neomorphic ibuprofen compositions containing the amorphous ibuprofen, the resolidification of the supercooled ibuprofen can be aided by the addition of amorphous ibuprofen. Such "seeding" techniques are particularly preferred when the processing temperature is below about 0° C. and kinetic energy is not used as the sole means for resolidification.

Birefringence is a characteristic common to crystalline materials. Birefringence is easily determined by viewing the material through partially or completely crossed polarized filters. Amorphous ibuprofen does not exhibit birefringence and is thus substantially colorless when viewed through partially or completely crossed polarized lenses. Conventional ibuprofen exhibits birefringence and displays various colors when viewed through crossed polarizers.

Differential scanning calorimetry can also be used to distinguish the neomorphic ibuprofen compositions from crystalline ibuprofen. The neomorphic ibuprofen compositions generally have a lower heat of fusion than similarly prepared crystalline ibuprofen samples.

The x-ray diffraction patterns for the neomorphic ibuprofen compositions of the present invention and conventional ibuprofen display peaks for the two types of ibuprofen at substantially similar positions, however, the intensities of these peaks are different. It is believed that the differences in the intensities is due to the distinct orientation and morphology of the surface of two polymorphs of ibuprofen.

Generally, the neomorphic ibuprofen compositions are chemically similar to conventional ibuprofen. The infrared spectra for the neomorphic and conventional forms of ibuprofen in a potassium bromide dispersion have substantially similar peak patterns.

Tests indicate that the neomorphic ibuprofen compositions of the present invention can be masticated and swallowed in their unaltered form without the bitter taste and burning sensation caused by conventional ibuprofen. The compositions can be presented as powders or as compressed tablets with or without a coating, both optionally being presentable within a capsule. The neomorphic form can therefore be administered without the need for taste-masking or flavor enhancing additives or agents. If desired, however, such components as well as other pharmaceutically acceptable carriers or diluents can be admixed with the neomorphic ibuprofen compositions to produce a pharmaceutical composition. Such pharmaceutical compositions of this invention include a therapeutically effective amount of the neomorphic ibuprofen and one or more pharmaceutical additives, carriers, or diluents. Such additives, carriers, and diluents are also well known in the art. For example, such additives as sweeteners such as sorbitol, dextrose, and synthetic sweeteners such as aspartame can be admixed with the compositions. Further, granulating agents such as sorbitol, mannitol, dextrose, sucrose, lactose and like sugars, starches, or mixtures thereof can also be admixed with the compositions to prepare tablets. Buffering agents such as the sodium, calcium or magnesium salts of bicarbonate and phosphate can be admixed with the compositions. Also rapid dispersal agents such as starches and celluloses, particularly pregelatinized corn starch, crospovidone, and croscarmellose sodium can be admixed with the compositions. Other additives such as flavorant, colorants, surfactants, and oils can also be admixed or blended with the compositions; lubricants such as magnesium stearate, talc, calcium stearate, stearic acid, and hydrogenated vegetable oils, and flow control agents such as microcrystalline cellulose, microcrystalline dextrose, amylose, and polyvinylpyrrolidone can be used. Further, the neomorphic ibuprofen compositions can be coated with a lipid that is a solid at about 22° C. such as described in application Ser. No. 889,179 filed May 27, 1992, U.S. Pat. No. 5,320,848 entitled Chewable Drug Delivery Composition, which is incorporated by reference herein in its entirety. The neomorphic ibuprofen compositions can also be prepared as liquid suspensions or dispersions, as gums, or any other known delivery form.

The neomorphic ibuprofen compositions of the present invention can be administered to animals using the same protocols as those used for conventional crystalline ibuprofen. Tests indicate that the amorphous ibuprofen is less irritating to the body of an animal in comparison with the crystalline form. This feature of the amorphous ibuprofen is highly advantageous for the administration of the ibuprofen via a mucosal route such as oral, rectal, or vaginal administration, especially to humans.

The preferred route of administration is oral. The neomorphic ibuprofen composition is believed to result in less irritation to the gastrointestinal tract of the animal and therefore leads to the lower occurrence of ulceration as compared to crystalline ibuprofen. This advantage over the crystalline ibuprofen allows for the administration of higher dosages, or more frequent dosings, of the neomorphic ibuprofen compositions. Patient comfort and safety may be improved which should also lead to better patient compliance.

The dosage to effect the desired therapeutic result, "therapeutically effective amount", for the neomorphic ibuprofen composition can be readily determined by those skilled in the art. Generally, ranges from about 100 mg to about 800 mg ibuprofen per dosage, which can be repeated about every 4 to 6 hours should provide acceptable responses. Ibuprofen is known to be useful in alleviating inflammatory conditions and pain associated therewith.

Pharmaceutical compositions comprising the neomorphic ibuprofen compositions and one or more other medicaments, preferably antihistamines, cough suppressants, decongestants, expectorants, and bronchodilators, can also be made. These medicaments are combined in therapeutically effective amounts which are well known in the art. For example, pseudoephedrine can be combined with the neomorphic ibuprofen compositions in ranges of about 5–25 mg pseudoephedrine per 100 mg neomorphic ibuprofen. Terfenadine can be combined with the neomorphic ibuprofen compositions, generally in ranges of about 5–50 mg terfenadine per 100 mg neomorphic ibuprofen. Also, pyrilamine maleate and chlorpheniramine maleate can be combined with the neomorphic ibuprofen compositions in ranges of about 0.5–10 mg of the maleate per 100 mg neomorphic ibuprofen. Further, phenyl propanolamine hydrochloride can be combined with the neomorphic ibuprofen compositions in ranges of about 1–10 mg of the hydrochloride per 100 mg neomorphic ibuprofen. Examples of bronchodilators include such compounds as thothylline. Examples of cough suppressants include such compounds as dextromethorphan hydrobromide. Examples of expectorants include such compounds as guaifenesin. Other commonly used additives that can be combined with these medicaments include such compounds as caffine and alcohols.

Pharmaceutical compositions comprising the neomorphic ibuprofen and other similar acting medicaments such as aspirin and acetaminophen can also be made. Generally the amount of aspirin or acetaminophen is in the range of about 25–200 mg per 100 mg neomorphic ibuprofen.

The various embodiments of the present invention are further described by the following non-limiting examples.

EXAMPLE 1

Conventional ibuprofen, about 2 g, manufactured by Ethyl Corporation, was heated to molten state at a temperature of about 77° C. to 80° C. and transferred into a pliable plastic container (2 ml). The container was then placed in an ice bath for about 10 minutes until the temperature of the now supercooled ibuprofen was about 0° C. The vessel was struck repeatedly by a hammer weighing about 0.5 kg to induce the supercooled ibuprofen to resolidify. The solidification proceeded and the hammering was continued for about 5 minutes until substantially all of the ibuprofen was resolidified. The resolidified amorphous ibuprofen was found to have a noticeably less bitter taste and produced relatively little burning sensation in the mouth and throat in comparison to conventional ibuprofen.

The x-ray diffraction pattern for the neomorphic ibuprofen composition containing the amorphous ibuprofen displayed minor peaks at about 2.64, 2.80, 2.89, 3.47, 3.70, 6.06, 6.36 and major peaks at about 4.02, 4.43, 4.53, 4.67, 5.03, 5.37, and 14.5. The x-ray diffraction pattern for a sample of crystalline ibuprofen displayed minor peaks at about 2.63, 2.80, 2.89, 7.25 and major peaks at about 3.96, 4.40, 4.67, 4.72, 5.33 and 14.5.

The infrared spectra, using a potassium bromide dispersion of the samples, for the neomorphic ibuprofen composition and crystalline ibuprofen were also very similar. The neomorphic ibuprofen composition displayed peaks as indicated in Table 1.1. The crystalline ibuprofen displayed peaks as indicated in Table 1.2.

TABLE 1.1

| $CM^{-1}$ | % | $CM^{-1}$ | % |
|---|---|---|---|
| 3822.3 | 33.11 | 1167.8 | 40.07 |
| 3448.2 | 25.87 | 1122.9 | 45.86 |
| 2955.9 | 14.12 | 1091.8 | 48.00 |
| 2868.2 | 16.98 | 1066.8 | 38.73 |
| 2728.2 | 27.45 | 1008.0 | 40.17 |
| 2631.9 | 28.45 | 969.9 | 44.84 |
| 2363.7 | 43.49 | 935.8 | 31.00 |
| 1720.5 | 14.12 | 880.1 | 50.39 |
| 1560.2 | 53.61 | 865.9 | 34.53 |
| 1507.9 | 30.12 | 849.1 | 46.93 |
| 1461.9 | 30.51 | 819.9 | 57.18 |
| 1450.8 | 38.17 | 779.6 | 24.06 |
| 1419.8 | 23.46 | 746.3 | 52.02 |
| 1379.6 | 34.27 | 690.9 | 51.98 |
| 1364.4 | 43.83 | 668.0 | 32.23 |
| 1320.9 | 28.96 | 636.2 | 46.88 |
| 1268.3 | 29.70 | 588.3 | 42.16 |
| 1231.0 | 20.4S | 521.8 | 40.89 |
| 1183.4 | 26.21 | 478.7 | 58.20 |

TABLE 1.2

| $CM^{-1}$ | % | $CM^{-1}$ | % |
|---|---|---|---|
| 2955.6 | 10.89 | 1067.3 | 39.29 |
| 2868.5 | 14.81 | 1007.9 | 40.25 |
| 2728.7 | 25.28 | 969.8 | 43.52 |
| 2631.9 | 26.42 | 935.6 | 30.38 |
| 2360.8 | 30.74 | 880.1 | 48.55 |
| 2341.8 | 33.97 | 865.9 | 35.03 |
| 1720.6 | 7.06 | 849.0 | 45.68 |
| 1560.2 | 52.15 | 819.8 | 54.33 |
| 1507.9 | 29.57 | 779.7 | 25.29 |
| 1462.0 | 30.40 | 746.2 | 49.62 |
| 1420.1 | 21.71 | 690.5 | 49.07 |
| 1379.8 | 33.68 | 668.1 | 29.70 |
| 1364.8 | 42.88 | 636.1 | 44.77 |
| 1321.1 | 27.24 | 588.3 | 41.35 |
| 1268.2 | 28.45 | 521.5 | 39.66 |
| 1231.0 | 16.69 | 478.5 | 52.85 |
| 1183.7 | 25.28 | | |
| 1123.1 | 44.78 | | |
| 1091.9 | 46.80 | | |

EXAMPLE 2

Example 1 was repeated using the same container having about 3 stainless steel (316) wire pieces (1 cm long, 0.1 cm diameter) placed into the container. Again the neomorphic ibuprofen composition containing the amorphous ibuprofen particles recovered after the hammering had an improved taste and a decreased burning sensation in comparison to the conventional ibuprofen.

EXAMPLE 3

Conventional ibuprofen (5 g) manufactured by Ethyl Corp., was heated to a temperature of about 77° C. to 80° C. in a plastic vessel to form molten ibuprofen. A lid was securely positioned onto the vessel. The vessel was then placed in an ice bath to cool the molten ibuprofen to the supercooled state at a temperature of about 0° C. The lid was removed and about 15 ml of glycerol was added to the vessel and the lid was resecured. The vessel was shaken vigorously by hand for about 10 minutes. The slurry was poured onto a vacuum filter (Durx 770, Berkshire Corp.) without disturbing the drug that adhered to the vessel walls. The ibuprofen filtered material was washed thoroughly with water to remove the glycerol. The final product was dried at

45° C.

The neomorphic ibuprofen was then sieved through a set of sieves to yield particles of about 500 microns and smaller. These neomorphic ibuprofen particles were found to have almost no burning sensation when tasted upon mastication and swallowing during oral administration.

EXAMPLE 4

Conventional ibuprofen (5 g) manufactured by Ethyl Corp., and 15 ml glycerol were heated in a water bath for about 15 minutes at a temperature of about 77° C. to 80° C. in a plastic vessel to form molten ibuprofen. A lid was securely positioned onto the vessel. The vessel was then placed in an ice bath to cool the molten ibuprofen to the supercooled state at a temperature of about 8° C. The vessel was shaken vigorously by hand for about 10 minutes. The slurry was poured onto a vacuum filter (Durx 770, Berkshire Corp.) without disturbing the drug that adhered to the vessel walls. The ibuprofen filtered material was washed thoroughly with water to remove the glycerol. The final product was dried at 45° C.

The neomorphic ibuprofen particles were found to have almost no burning sensation when tasted upon mastication and swallowing during oral administration.

EXAMPLE 5

Approximately one gram ibuprofen (BHC Corporation, Corpus Christi, Tex.) was placed in the bottom of a tall glass vial (height approx. 4.25 inches) while avoiding contact of the ibuprofen with the walls of the vial. The vial was then capped and heated in a water bath at around 88° C. to 91° C.

The vial was allowed to float in the water bath without touching the hot base of the bath, so that the material within would not be exposed to extremely high temperatures. The vial remained in this environment until all the ibuprofen melted. Once this had occurred, the vial was placed in a freezer at −20° C. Spontaneous solidification into a few opaque particles was seen to occur in time. The number of solidified particles was found to increase with time. Eventually, all the material was seen to have solidified. The vial and its contents were allowed to remain in that environment for 24 to 48 hours without being disturbed.

Some material was taken from the solidified mass and observed under a microscope. Under crossed polarized filters, it was seen to be dull and to have very little birefringence. Some material on the slide was gently crushed with a spatula. The crushed particles were also seen to have very little birefringence. The particles were found to have no bad taste or burning sensation on the tongue, throat and lips even upon chewing the particles.

EXAMPLE 6

The same procedure as in Example 1 was carried out through the melting stage. The vial was then placed in a glycerol bath maintained at −20° C., and the vial was swirled to mix the molten ibuprofen inside, while the ibuprofen viscosity was low. The viscosity was seen to increase as the temperature of the molten ibuprofen decreased. The vial was allowed to rest in the chilled glycerol bath for about two hours and was then placed in the freezer at −20° C. The subsequent procedure and testing of the material was performed in the same way as in Example t. Upon testing the produced material under the microscope, it was found to comprise mainly non-birefringent particles.

EXAMPLE 7

The procedure was the same as in Example 1, except that, after melting and chilling, the highly viscous fluid ibuprofen was stirred. The stirring rod used was made of glass and its temperature was also at −20° C. because it had been maintained in the freezer, in order to have it at the same temperature as the bulk of the material. The material was found to solidify much faster than in Example 1. Upon testing the produced material under the microscope, it was found to comprise mainly non-birefringent particles.

EXAMPLE 8

After the melting and chilling as described in Example 1, the chilled material was seeded with some preformed resolidified neomorphic ibuprofen made in accordance with Example 1. The seeding was performed by placing 2–3 particles of neomorphic ibuprofen onto the surface of the bulk ibuprofen after melting and chilling the bulk ibuprofen. Relative to Example 1, the resolidification of the bulk into particles of the neomorphic form was found to proceed at a faster rate.

EXAMPLE 9

Experiments were conducted to compare gastric mucosal ulcers caused by oral capsule dosage of conventional crystalline ibuprofen versus the neomorphic ibuprofen compositions of the present invention in male Sprague-Dawley rats.

The neomorphic ibuprofen composition was prepared by the procedure set forth in Example 3 and passed through a 100 mesh sieve (150 µm opening), using the material that passed through the sieve. The conventional ibuprofen used was 50 micron grade ibuprofen from Hoechst Celanese.

Individual capsules were filled with the respective form of ibuprofen. Placebo capsules were filled with dextrose powder (Spectrum Chemical Mfg. Corp.). Each capsule was weighed to determine the amount of drug per capsule.

A total of 53 male Sprague-Dawley rates, weighing 181–292 g were fasted 18 hours prior to the experiment. Animals were maintained in cages on wire mesh supports throughout the fasting period and the remainder of the experiment. Animals were divided into the following groups and dosed, p.o., at t=0.

The animals were divided into three groups:

Group 1: (placebo) Eight animals (189–291 g) dosed 1 dextrose capsule/rat.

Group 2: (conventional ibuprofen) Twenty two animals (181–292 g) dosed 1 conventional ibuprofen capsule/rat, average dosing was 62.8 mg ibuprofen/kg animal.

Group 3: (neomorphic ibuprofen composition) Twenty three animals (188–280 g) dosed 1 neomorphic ibuprofen composition capsule/rat, average dosing was 57.5 mg ibuprofen/kg animal.

All rats were placed into the cage after administration and deprived of food and water for 120 minutes. After the 120 minute test period, the animals were sacrificed with 0.4 ml of pentobarbital i.p. for euthanasia. Necropsies were then performed to evaluate the stomach for ulcers in the gastric mucosa. Ulcer was used to denote a visible, discrete, damaged, "crater-like" area of the mucosa that was brown to black in color. Ulcers detected visually were greater than about 1 mm in diameter.

The results of the necropsies are shown in Table 9.1. The mean ulcers/rat for the conventional ibuprofen was 9.1 and for the neomorphic composition it was 4.6. The standard deviation for the number of ulcers was 10.1 for the conventional ibuprofen and 4.4 for the neomorphic composition. The t-statistic for the experiment was 1.96 and the p value was 0.028.

TABLE 9.1

| Number of Ulcers at 120 Min. | Conventional Ibuprofen | | Neomorphic Ibuprofen | |
|---|---|---|---|---|
| | # Rats | % of Total | # Rats | % of Total |
| 0 | 5 | 22.7 | 8 | 34.8 |
| 1–5 | 6 | 27.3 | 6 | 26.1 |
| 6–10 | 2 | 9.1 | 5 | 21.7 |
| 11–15 | 3 | 13.6 | 4 | 17.4 |
| 16–20 | 4 | 18.2 | 0 | 0 |
| 21–25 | 1 | 4.5 | 0 | 0 |
| 26–30 | 0 | 0 | 0 | 0 |
| 31–35 | 0 | 0 | 0 | 0 |
| 36–40 | 1 | 4.5 | 0 | 0 |

EXAMPLE 10

Differential scanning calorimetry (DSC) experiments were conducted to compare the neomorphic ibuprofen of the present invention to conventional crystalline ibuprofen. All samples were heated from 25°–90° C. at a rate of 10° C./min.

Conventional ibuprofen, 38 μm sized, from Hoechst Celanese had a melting point onset of 75.1° C. and the heat of fusion was 124.5 J/g.

A neomorphic ibuprofen composition prepared by the procedure set forth in Example 1 had a melting point onset of 72.1° C. and the heat of fusion was 118.7 J/g.

A neomorphic ibuprofen composition prepared by the procedure set forth in Example 3 had a melting point onset of 71.1° C. and the heat of fusion was 119.3 J/g.

Another neomorphic ibuprofen composition also prepared by the procedure set forth in Example 3 had a melting point onset of 70.6° C. and the heat of fusion was 119.5 J/g.

EXAMPLE 11

A dissolution study was conducted to determine the rates of dissolution between conventional ibuprofen and the neomorphic ibuprofen composition. The conventional crystalline ibuprofen used was 38 μm ibuprofen from Hoechst Celanese. The neomorphic ibuprofen composition was that as described in Example 9.

About 100 mg of the ibuprofen powders, six samples of each, were placed in a basket suspended in 900 ml of phosphate buffer (pH 7.2). The buffer solution temperature was maintained at 37.3° C. Samples were spun at 150 rpm for 30 minutes using a standard USP dissolution apparatus.

A sample of dissolution medium was removed after 30 minutes to determine the concentration of ibuprofen by UV spectroscopy. The percentage of the drug released based on the amount present was then determined. The average release for the six samples was 95.6% for conventional ibuprofen and 95.4% for the neomorphic ibuprofen composition. The standard deviation for the conventional ibuprofen was 4.0% and 5.2% for the neomorphic composition.

What is claimed is:

1. A method of treating an animal for the reduction of pain, fever, or for an inflammatory condition, comprising administering to an animal a therapeutically effective amount of a neomorphic ibuprofen composition comprising amorphous ibuprofen.

2. The method of claim 1 wherein said administration is either orally, rectally, or vaginally.

3. The method of claim 1 wherein said administration is orally.

4. The method of claim 1 wherein said amorphous ibuprofen exhibits no birefringence.

5. The method of claim 1 wherein said amorphous ibuprofen comprises at least about 50 percent by weight of said neomorphic ibuprofen composition.

6. The method of claim 5 further comprising admixing with said neomorphic ibuprofen composition one or more pharmaceutically acceptable additives, diluents, or carriers to form a pharmaceutical composition and administering said pharmaceutical composition.

7. The method of claim 5 wherein said amorphous ibuprofen exhibits no birefringence.

8. The method of claim 5 further comprising admixing pseudoephedrine with said neomorphic ibuprofen composition to form a pharmaceutical composition and administering said pharmaceutical composition.

9. The method of claim 5 further comprising admixing pyrilamine maleate with said neomorphic ibuprofen composition to form a pharmaceutical composition and administering said pharmaceutical composition.

10. The method of claim 5 further comprising admixing aspirin or acetaminophen with said neomorphic ibuprofen composition to form a pharmaceutical composition and administering said pharmaceutical composition.

11. The method of claim 5 further comprising admixing an antihistamine with said neomorphic ibuprofen composition to form a pharmaceutical composition and administering said pharmaceutical composition.

12. The method of claim 11 wherein said antihistamine comprises terfenadine.

13. The method of claim 1 wherein said amorphous ibuprofen comprises at least about 70 percent by weight of said neomorphic ibuprofen composition.

14. The method of claim 13 wherein said amorphous ibuprofen exhibits no birefringence.

15. The method of claim 1 wherein said amorphous ibuprofen comprises at least about 90 percent by weight of said neomorphic ibuprofen composition.

16. The method of claim 15 wherein said amorphous ibuprofen exhibits no birefringence.

17. A neomorphic ibuprofen composition comprising ibuprofen, wherein said ibuprofen is at least about 90 percent by weight amorphous ibuprofen.

18. The neomorphic ibuprofen composition of claim 17 wherein said amorphous ibuprofen exhibits no birefringence.

19. The neomorphic ibuprofen composition of claim 17, wherein said ibuprofen is at least about 95 percent by weight amorphous ibuprofen.

20. The neomorphic ibuprofen composition of claim 19 wherein said amorphous ibuprofen exhibits no birefringence.

21. A pharmaceutical composition comprising (a) a therapeutically effective amount of neomorphic ibuprofen comprising amorphous ibuprofen and (b) one or more pharmaceutically acceptable additives, diluents, or carriers.

22. The pharmaceutical composition of claim 21 wherein said amorphous ibuprofen constitutes at least about 50 weight percent of the ibuprofen in said composition.

23. A pharmaceutical composition comprising (a) a therapeutically effective amount of neomorphic ibuprofen comprising amorphous ibuprofen and (b) a therapeutically effective amount of acetaminophen or aspirin.

24. The pharmaceutical composition of claim 23 wherein said amorphous ibuprofen constitutes at least about 50 weight percent of the ibuprofen in said composition.

25. A pharmaceutical composition comprising (a) a therapeutically effective amount of neomorphic ibuprofen comprising amorphous ibuprofen and (b) a therapeutically effective amount of one or more other medicaments comprising antihistamines, cough suppressants, decongestants, expectorants, and bronchodilators.

26. The pharmaceutical composition of claim 25 wherein said amorphous ibuprofen constitutes at least about 50 weight percent of the ibuprofen in said composition.

27. The method of claim 5 wherein said administration is orally.

28. The method of claim 7 wherein said administration is orally.

29. The method of claim 13 wherein said administration is orally.

30. The method of claim 14 wherein said administration is orally.

* * * * *